(12) United States Patent
Yanagawa et al.

(10) Patent No.: US 10,087,376 B2
(45) Date of Patent: *Oct. 2, 2018

(54) METHOD FOR PRODUCING MONOCYCLIC AROMATIC HYDROCARBONS

(71) Applicant: JX Nippon Oil & Energy Corporation, Tokyo (JP)

(72) Inventors: Shinichiro Yanagawa, Kanagawa (JP); Masahide Kobayashi, Kanagawa (JP); Kazuaki Hayasaka, Kanagawa (JP)

(73) Assignee: JX Nippon Oil & Energy Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/801,089

(22) Filed: Jul. 16, 2015

(65) Prior Publication Data

US 2015/0322352 A1 Nov. 12, 2015

Related U.S. Application Data

(62) Division of application No. 13/522,867, filed as application No. PCT/JP2011/050995 on Jan. 20, 2011.

(30) Foreign Application Priority Data

Jan. 20, 2010 (JP) .................. 2010-010262

(51) Int. Cl.
| | | |
|---|---|---|
| *C07C 4/06* | (2006.01) | |
| *C10G 11/05* | (2006.01) | |
| *B01J 29/80* | (2006.01) | |
| *C10G 47/16* | (2006.01) | |
| *C10G 11/18* | (2006.01) | |
| *B01J 29/08* | (2006.01) | |
| *B01J 29/18* | (2006.01) | |
| *B01J 29/40* | (2006.01) | |
| *B01J 29/70* | (2006.01) | |
| *B01J 37/00* | (2006.01) | |

(52) U.S. Cl.
CPC .............. *C10G 11/05* (2013.01); *B01J 29/80* (2013.01); *C07C 4/06* (2013.01); *C10G 11/18* (2013.01); *C10G 47/16* (2013.01); *B01J 29/084* (2013.01); *B01J 29/18* (2013.01); *B01J 29/40* (2013.01); *B01J 29/405* (2013.01); *B01J 29/7007* (2013.01); *B01J 29/7057* (2013.01); *B01J 37/0009* (2013.01); *B01J 2229/36* (2013.01); *B01J 2229/37* (2013.01); *C07C 2529/06* (2013.01); *C07C 2529/08* (2013.01); *C07C 2529/40* (2013.01); *C10G 2300/107* (2013.01); *C10G 2300/1033* (2013.01); *C10G 2300/1044* (2013.01); *C10G 2300/1048* (2013.01); *C10G 2300/1051* (2013.01); *C10G 2300/1055* (2013.01); *C10G 2300/1059* (2013.01); *C10G 2300/301* (2013.01); *C10G 2400/02* (2013.01); *C10G 2400/20* (2013.01); *C10G 2400/30* (2013.01)

(58) Field of Classification Search
USPC ........................................................ 585/476
See application file for complete search history.

(56) References Cited

U.S. PATENT DOCUMENTS

| | | | |
|---|---|---|---|
| 2,727,854 A | 12/1955 | Brown et al. | |
| 2,769,753 A | 11/1956 | Hutchings | |
| 3,258,503 A | 6/1966 | Drehman et al. | |
| 3,755,141 A | 8/1973 | Youngblood et al. | |
| 3,806,443 A | 4/1974 | Maziuk | |
| 3,847,793 A * | 11/1974 | Schwartz .................. | B01J 8/26 |
| | | | 208/164 |
| 3,926,778 A | 12/1975 | Owen et al. | |
| 4,053,388 A | 10/1977 | Bailey | |
| 4,309,280 A | 1/1982 | Rosinski et al. | |
| 4,585,545 A | 4/1986 | Yancey, Jr. et al. | |
| 4,762,813 A | 8/1988 | Ward | |
| 5,002,915 A | 3/1991 | Harandi et al. | |
| 5,143,596 A | 9/1992 | Maxwell et al. | |
| 5,183,557 A | 2/1993 | Degnan, Jr. et al. | |
| 5,582,711 A | 12/1996 | Ellis et al. | |
| 5,905,051 A | 5/1999 | Domokos et al. | |
| 5,981,418 A | 11/1999 | Drake et al. | |
| 6,124,515 A | 9/2000 | Wu et al. | |
| 6,210,563 B1 | 4/2001 | Tsao et al. | |

(Continued)

FOREIGN PATENT DOCUMENTS

| | | |
|---|---|---|
| CN | 86101990 A | 10/1987 |
| CN | 101376823 A | 3/2009 |

(Continued)

OTHER PUBLICATIONS

Int'l Search Report dated Apr. 26, 2011 in Int'l Application No. PCT/JP2011/050995.

Extended European Search Report dated Feb. 4, 2014 in EP Application No. 11734727.8.

Office Action dated Apr. 2, 2015 in U.S. Appl. No. 13/522,867.

(Continued)

*Primary Examiner* — Elizabeth D Wood

(74) *Attorney, Agent, or Firm* — Panitch Schwarze Belisario & Nadel LLP

(57) ABSTRACT

A catalyst is provided for production of monocyclic aromatic hydrocarbons having a carbon number of 6 to 8 from feedstock in which a 10 vol % distillation temperature is 140° C. or higher and a 90 vol % distillation temperature is 380° C. or lower. The catalyst contains crystalline aluminosilicate including large-pore zeolite having a 12-membered ring structure, and intermediate-pore zeolite having a 10-membered ring structure.

8 Claims, No Drawings

(56) References Cited

U.S. PATENT DOCUMENTS

| | | | |
|---|---|---|---|
| 7,553,791 B2 | 6/2009 | McMinn et al. | |
| 8,846,995 B2* | 9/2014 | Yanagawa | C10G 69/08 |
| | | | 208/66 |
| 8,912,377 B2 | 12/2014 | Kim et al. | |
| 9,200,217 B2* | 12/2015 | Sagawa | C10L 1/08 |
| 9,233,892 B2* | 1/2016 | Yanagawa | C10G 69/10 |
| 2003/0019792 A1 | 1/2003 | Chen et al. | |
| 2003/0171634 A1 | 9/2003 | Corma | |
| 2004/0140246 A1 | 7/2004 | Lomas | |
| 2004/0215042 A1 | 10/2004 | Bottcher et al. | |
| 2005/0234279 A1 | 10/2005 | Serra et al. | |
| 2006/0014630 A1 | 1/2006 | Matsumoto et al. | |
| 2006/0207917 A1 | 9/2006 | Domokos et al. | |
| 2007/0144942 A1 | 6/2007 | Tiitta et al. | |
| 2007/0209969 A1 | 9/2007 | Shen et al. | |
| 2007/0227946 A1* | 10/2007 | Dierickx | C10G 11/00 |
| | | | 208/113 |
| 2008/0093263 A1 | 4/2008 | Cheng et al. | |
| 2008/0256846 A1 | 10/2008 | Yoshida et al. | |
| 2008/0293561 A1 | 11/2008 | Long et al. | |
| 2009/0112034 A1 | 4/2009 | Levin | |
| 2009/0288985 A1 | 11/2009 | Long et al. | |
| 2010/0016645 A1 | 1/2010 | Cosyns et al. | |
| 2010/0145127 A1 | 6/2010 | Xie et al. | |
| 2011/0056870 A1 | 3/2011 | Rispoli et al. | |
| 2011/0270005 A1 | 11/2011 | Yanagawa et al. | |
| 2012/0012504 A1 | 1/2012 | Minami et al. | |
| 2013/0015102 A1 | 1/2013 | Yanagawa et al. | |

FOREIGN PATENT DOCUMENTS

| | | |
|---|---|---|
| CN | 101570698 A | 11/2009 |
| CN | 102458657 A | 5/2012 |
| CN | 102470352 A | 5/2012 |
| CN | 102811814 A | 12/2012 |
| CN | 102858922 A | 1/2013 |
| EP | 0600686 A1 | 6/1994 |
| EP | 0911308 A1 | 4/1999 |
| EP | 1762299 A1 | 3/2007 |
| EP | 2072604 A1 | 6/2009 |
| EP | 2351820 A2 | 8/2011 |
| JP | S49-41323 A | 4/1974 |
| JP | S53-116328 A | 10/1978 |
| JP | 02-184517 A | 7/1990 |
| JP | 03-002128 A | 1/1991 |
| JP | 03-026791 A | 2/1991 |
| JP | 03-052993 A | 3/1991 |
| JP | H03-177496 A | 8/1991 |
| JP | 04-504577 T | 8/1992 |
| JP | H05-64743 A | 3/1993 |
| JP | 06-220466 A | 8/1994 |
| JP | H08508970 A | 9/1996 |
| JP | H08-277396 A | 10/1996 |
| JP | H09-263775 A | 10/1997 |
| JP | H1036860 A | 2/1998 |
| JP | 2001-098288 A | 4/2001 |
| JP | 2002-146364 A | 5/2002 |
| JP | 2002-530475 A | 9/2002 |
| JP | 2003-502478 A | 1/2003 |
| JP | 2003-096474 A | 4/2003 |
| JP | 2006-028493 A | 2/2006 |
| JP | 2006-083254 A | 3/2006 |
| JP | 2006-137922 A | 6/2006 |
| JP | 2007-512127 A | 5/2007 |
| JP | 2007-154151 A | 6/2007 |
| JP | 2008-508084 A | 3/2008 |
| JP | 2008-138188 A | 6/2008 |
| JP | 2008-144158 A | 6/2008 |
| JP | 2008-518778 A | 6/2008 |
| JP | 2008-214369 A | 9/2008 |
| JP | 2008-239877 A | 10/2008 |
| JP | 2008-248175 A | 10/2008 |
| JP | 2008-297452 A | 12/2008 |
| JP | 2008-545035 A | 12/2008 |
| JP | 2009-073919 A | 4/2009 |
| JP | 2009079172 A | 4/2009 |
| JP | 2009516015 A | 4/2009 |
| JP | 2009-167257 A | 7/2009 |
| JP | 2009-227933 A | 10/2009 |
| JP | 2009-235247 A | 10/2009 |
| JP | 2009-235248 A | 10/2009 |
| JP | 2010-001462 A | 1/2010 |
| JP | 2010-001463 A | 1/2010 |
| JP | 2010-070732 A | 4/2010 |
| JP | 2011190306 A | 9/2011 |
| JP | 2012-062255 A | 3/2012 |
| JP | 2012062356 A | 3/2012 |
| JP | 2012241174 A | 12/2012 |
| JP | 2013014760 A | 1/2013 |
| KR | 20010012397 A | 2/2001 |
| WO | 9108998 A1 | 6/1991 |
| WO | 9521693 A1 | 8/1995 |
| WO | 0029517 A1 | 5/2000 |
| WO | 2007003709 A1 | 1/2007 |
| WO | 2007055488 A1 | 5/2007 |
| WO | 2009041508 A1 | 4/2009 |
| WO | 2010044562 A2 | 4/2010 |
| WO | 2010109899 A1 | 9/2010 |
| WO | 2011090124 A1 | 7/2011 |
| WO | 2011118753 A1 | 9/2011 |
| WO | 2012091092 A1 | 7/2012 |
| WO | 2012133138 A1 | 10/2012 |
| WO | 2012133170 A1 | 10/2012 |
| WO | 2012133197 A1 | 10/2012 |
| WO | 2012161281 A1 | 11/2012 |
| WO | 2012169651 A1 | 12/2012 |

OTHER PUBLICATIONS

Decision of Rejection dated Nov. 4, 2015 in JP Application No. 2011505307.

Office Action dated Oct. 25, 2016 in JP Application No. 2016-019280.

Office Action dated Oct. 19, 2016 in CN Application No. 201480009592.1.

Office Action dated Dec. 12, 2016 in EP Application No. 11734727.8.

Office Action dated Feb. 18, 2016 in U.S. Appl. No. 13/822,556 by Yanagawa.

Final Office Action dated Oct. 7, 2016 in U.S. Appl. No. 13/822,556 by Yanagawa.

Int'l Search Report dated Jun. 5, 2012 in Int'l Application No. PCT/JP2012/057537.

Extended European Search Report dated Aug. 4, 2014 in EP Application No. 12765326.9.

Office Action dated Sep. 25, 2015 in U.S. Appl. No. 14/007,193 by Yanagawa.

Int'l Search Report dated Jul. 3, 2012 in Int'l Application No. PCT/JP2012/062311.

Seiichi, "Nenryo Kogaku Gairon," Shokabo Publishing Co., pp. 136-144 (Mar. 1991).

International Search Report dated May 20, 2014 in International Application No. PCT/JP2014/054178.

"Petrochemical Process," The Japan Petroleum Institute, Kodansha Ltd., pp. 21-30 (Aug. 10, 2001).

Office Action dated Mar. 9, 2016 in CN Application No. 201480009592.1.

Hao et al., "Effects of Steaming Treatment on the Structure and Reaction Stability of Catalysts for C4 Producing Aromatics," Acta Petrolei Sinica (Petroleum Processing Section), pp. 206-209 (Oct. 31, 2006).

Guiru, "Catalyst and Catalysis," Dalian University of Technology Press, p. 339 (Aug. 31, 2000).

Speight, James G, "Thermal cracking of petroleum," Natural and Laboratory-Simulated Thermal Geochemical Processes, Springer Netherlands, pp. 31-52 (2003).

Speight, James G., ed, "Petroleum Chemistry and Refining," CRC Press (1997).

(56) References Cited

OTHER PUBLICATIONS

Rase, Howard F., "Handbook of Commercial Catalysts: Heterogeneous Catalysts," CRC press (2000).
Office Action dated Sep. 23, 2016 in U.S. Appl. No. 14/769,491 by Iwasa.
Int'l Search Report dated Jun. 26, 2012 in Int'l Application No. PCT/JP2012/062312.
Nomura, "Hakuyo nenryo no Kagaku," Hirotsugu, pp. 164-166 (1994).
Extended European Search Report dated Oct. 1, 2014 in EP Application No. 12789718.9.
Office Action dated Dec. 31, 2015 in U.S. Appl. No. 14/117,241 by Mitsui.
American Petroleum Institute Petroleum HPV Testing Group, "Robust Summary of Information on Heavy Fuel Oil Category," pp. 1-7 (2003).
Final Office Action dated Jul. 27, 2016 in U.S. Appl. No. 14/117,241 by Mitsui.
Int'l Search Report dated Jun. 5, 2012 in Int'l Application No. PCT/JP2012/057487.
Extended European Search Report dated Aug. 4, 2014 in EP Application No. 12762799.0.
Office Action dated Oct. 7, 2014 in JP Application No. 2011-067692.
Int'l Search Report dated Nov. 8, 2011 in Int'l Application No. PCT/JP2011/070925.
Office Action dated Mar. 6, 2014 in CN Application No. 201180043781.7.
Extended European Search Report dated May 8, 2014 in EP Application No. 11825182.6.
Matsushita et al, "Development of BTX production technology from heavier fractions by selective hydrocracking," The Aromatics, vol. 61, pp. 221-225 (2009).
Int'l Search Report dated May 10, 2011 in Int'l Application No. PCT/JP2011/057299.
Office Action dated Dec. 30, 2013 in CN Application No. 201180016142.1.
Search Report dated Apr. 9, 2014 in EP Application No. 11759557.9.
Office Action dated Dec. 18, 2014 in U.S. Appl. No. 13/822,556 by Yanagawa.
Kaduk et al, "Crystal Structure of Zeolite Y as a Function of Ion Exchange," The Rigaku Journal, vol. 2, No. 2 (1995).
Gangwer, T., "Transfer of Hydrogen by Hydroaromatics. 1. Mechnaism of Dehydrogenation/Hydrogenation in Tetralin/Iron Catalyst Systems," J. Phys. Chem., vol. 84, pp. 2436-2441 (1980).
Advisory Action dated Oct. 4, 2016 in U.S. Appl. No. 14/117,241 by Mitsui.
Kaduk et al, "Crystal Structure of Zeolite Y as a Function of Ion Exchange," The Rigaku Journal, vol. 12, No. 2 (1995).
Office Action dated Jan. 25, 2017 in U.S. Appl. No. 14/769,491, by Iwasa.
Shafer et al, "Chemical Class Composition of Commercial Jet Fuels and Other Specialty Kerosene Fuels," Space Planes and Hypersonic Systems and Technologies Conference, American Institute of Aeronautics and Astronautics, Nov. 2006.
Office Action dated Jan. 18, 2017 in KR Application No. 10-2012-7021322.
Office Action dated May 18, 2017 in U.S. Appl. No. 14/769,491, by Iwasa.

\* cited by examiner

METHOD FOR PRODUCING MONOCYCLIC AROMATIC HYDROCARBONS

CROSS-REFERENCE TO RELATED APPLICATION

This application is a divisional of U.S. application Ser. No. 13/522,867 filed Oct. 12, 2012, now abandoned, which is a Section 371 of International Application No. PCT/JP2011/050995, filed Jan. 20, 2011, which was published in the Japanese language on Jul. 28, 2011 under International Publication No. WO 2011/090121 A1, and the disclosures of which are incorporated herein by reference.

TECHNICAL FIELD

The present invention relates to a catalyst for producing monocyclic aromatic hydrocarbons and a method of producing monocyclic aromatic hydrocarbons, which are capable of producing monocyclic aromatic hydrocarbons from oil containing a large amount of polycyclic aromatic hydrocarbons.

Priority is claimed on Japanese Patent Application No. 2010-010262, filed Jan. 20, 2010, the content of which is incorporated herein by reference.

BACKGROUND ART

Light cycle oil (hereinafter, referred to as "LCO"), which is cracked light oil produced by a fluidized catalytic cracking, contains a large amount of polycyclic aromatic hydrocarbons, and has been used as light oil or heavy oil. However, in recent years, investigations have been conducted to obtain, from LCO, monocyclic aromatic hydrocarbons having a carbon number of 6 to 8 (such as benzene, toluene, xylene and ethylbenzene), which may be used as high-octane gasoline base materials or petrochemical raw materials, and offer significant added value.

For example, Patent Document 1 to Patent Document 3 disclose methods of producing monocyclic aromatic hydrocarbons from polycyclic aromatic hydrocarbons contained in large amounts within LCO and the like by using zeolite catalysts.

In addition, as a method of producing monocyclic aromatic hydrocarbons through reaction using zeolite catalysts, Patent Document 4 discloses a method of producing monocyclic aromatic hydrocarbons from aromatic compounds having a carbon number of 9 or more by using beta-type zeolite, which has a 12-membered ring structure and a large pore size, as a catalyst.

Patent Document 5 discloses a method of producing monocyclic aromatic hydrocarbons from paraffin-based hydrocarbons having a carbon number of 2 to 12 by using beta-type zeolite as a catalyst.

CITATION LIST

Patent Document

[Patent Document 1] Japanese Unexamined Patent Application, First publication No. H3-2128

[Patent Document 2] Japanese Unexamined Patent Application, First publication No. H3-52993 [Patent Document 3] Japanese Unexamined Patent Application, First publication No. H3-26791

[Patent Document 4] Published Japanese Translation No. H4-504577 of the PCT International Publication

[Patent Document 5] Japanese Unexamined Patent Application, First publication No. H2-184517

DISCLOSURE OF INVENTION

Technical Problem

However, in the methods disclosed in Patent Document 1 to Patent Document 3, the yields of monocyclic aromatic hydrocarbons having a carbon number of 6 to 8 have not been entirely satisfactory. In addition, the methods disclosed in Patent Document 4 and Patent Document 5 are not methods of obtaining both monocyclic aromatic hydrocarbons having a carbon number of 6 to 8 and aliphatic hydrocarbons having a carbon number of 3 to 4 from feedstock in which a 10 vol % distillation temperature is 140° C. or higher and a 90 vol % distillation temperature is 380° C. or lower.

An object of the invention is to provide a catalyst for production of monocyclic aromatic hydrocarbons and a method of producing monocyclic aromatic hydrocarbons, which are capable of producing monocyclic aromatic hydrocarbons having a carbon number of 6 to 8 from feedstock containing polycyclic aromatic hydrocarbons with high yield.

Solution to Problem (1) According to an embodiment of the invention, a catalyst is provided for production of monocyclic aromatic hydrocarbons having a carbon number of 6 to 8 from feedstock in which a 10 vol % distillation temperature is 140° C. or higher and a 90 vol % distillation temperature is 380° C. or lower. The catalyst contains crystalline aluminosilicate including large-pore zeolite having a 12-membered ring structure, and intermediate-pore zeolite having 10-membered ring structure.

(2) The catalyst for production of monocyclic aromatic hydrocarbons according to (1), wherein in the crystalline aluminosilicate, a mass ratio of the large-pore zeolite to the intermediate-pore zeolite (large-pore zeolite/intermediate-pore zeolite) is preferably 2/98 to 50/50.

(3) The catalyst for production of monocyclic aromatic hydrocarbons according to (1) or (2), wherein the large-pore zeolite is preferably a zeolite of any type selected from a BEA type, an FAU type, and an MOR type.

(4) The catalyst for production of monocyclic aromatic hydrocarbons according to any one of (1) to (3), wherein the large-pore zeolite is preferably BEA-type zeolite.

(5) The catalyst for production of monocyclic aromatic hydrocarbons according to any one of (1) to (4), wherein the intermediate-pore zeolite is preferably MFI-type zeolite.

(6) The catalyst for production of monocyclic aromatic hydrocarbons according to any one of (1) to (5), wherein the catalyst preferably further contain phosphorus.

(7) According to another embodiment of the invention, a method is provided of producing monocyclic aromatic hydrocarbons having a carbon number of 6 to 8. The method includes bringing feedstock in which a 10 vol % distillation temperature is 140° C. or higher and a 90 vol % distillation temperature is 380° C. or lower into contact with the catalyst for production of monocyclic aromatic hydrocarbons according to any one of (1) to (6).

(8) The method of producing monocyclic aromatic hydrocarbons having a carbon number of 6 to 8 according to (7), wherein as the feedstock, light cycle oil produced by a fluidized catalytic cracking is preferably used.

(9) The method of producing monocyclic aromatic hydrocarbons having a carbon number of 6 to 8 according to (7) or (8), wherein the feedstock is preferably brought into contact with the catalyst for production of monocyclic aromatic hydrocarbons in a fluidized bed reaction unit.

Advantageous Effects of Invention

According to the catalyst for production of monocyclic aromatic hydrocarbons and the method of producing monocyclic aromatic hydrocarbons having a carbon number of 6 to 8, monocyclic aromatic hydrocarbons having a carbon number of 6 to 8 is preferably produced with high yield from feedstock in which a 10 vol % distillation temperature is 140° C. or higher and a 90 vol % distillation temperature is 380° C. or lower.

BEST MODE FOR CARRYING OUT THE INVENTION (Catalyst for Production of Monocyclic Aromatic Hydrocarbon)

The catalyst for production of monocyclic aromatic hydrocarbons according to this embodiment (hereinafter, abbreviated as "catalyst") is used for producing monocyclic aromatic hydrocarbons having a carbon number of 6 to 8 (hereinafter, abbreviated as "monocyclic aromatic hydrocarbons") from feedstock containing polycyclic aromatic hydrocarbons and saturated hydrocarbons, and contains crystalline aluminosilicate.

(Crystalline Aluminosilicate)

In this embodiment, the crystalline aluminosilicate contains large-pore zeolite having a 12-membered ring structure, and intermediate-pore zeolite having a 10-membered ring structure.

As the large-pore zeolite having a 12-membered ring structure, for example, zeolites having a framework type of an AFI type, an ATO type, a BEA type, a CON type, an FAU type, a GME type, an LTL type, an MOR type, an MTW type, and an OFF type is preferably exemplified. Among these, the BEA type, the FAU type, and the MOR type are preferable from an industrially usable aspect, and the BEA type is more preferable because the yield of the monocyclic aromatic hydrocarbons having a carbon number of 6 to 8 is relatively raised.

As the intermediate-pore zeolite having a 10-membered ring structure, for example, zeolites having a framework type of an AEL type, an EUO type, an FER type, an HEU type, an MEL type, an MFI type, an NES type, a TON type, and a WEI type is preferably exemplified. Among these, the MFI type is preferable because the yield of the monocyclic aromatic hydrocarbons having a carbon number of 6 to 8 is relatively raised.

In addition, all of the framework type types of the zeolite, which are exemplified in this embodiment, are structure codes based on the definition of the International Zeolite Association.

In addition to the large-pore zeolite, the crystalline aluminosilicate may contain small-pore zeolite having a structure of a 10-membered ring or less, and ultra-large-pore zeolite having a structure of a 14-membered ring or more.

Here, as the small-pore zeolite, for example, zeolites having a framework type of an ANA type, a CHA type, an ERI type, a GIS type, a KFI type, an LTA type, an NAT type, a PAU type, and a YUG type is preferably exemplified.

As the ultra-large-pore zeolite, for example, zeolites having a framework type of a CLO type, and a VPI type is preferably exemplified.

In a case where the catalyst is used as a catalyst for a fixed bed, the content of the crystalline aluminosilicate is preferably 60 to 100% by mass on the basis of 100% by mass of the entirety of the catalyst, and more preferably 70 to 100% by mass, and still more preferably 90 to 100% by mass. When the content of the crystalline aluminosilicate is 60% by mass or more, the total yield of the monocyclic aromatic hydrocarbons having a carbon number of 6 to 8 and the aliphatic hydrocarbons having a carbon number of 3 to 4 is sufficiently raised.

In a case where the catalyst is used as a catalyst for a fluidized bed, the content of the crystalline aluminosilicate is preferably 20 to 60% by mass on the basis of 100% by mass of the entirety of the catalyst, and more preferably 30 to 60% by mass, and still more preferably 35 to 60% by mass. When the content of the crystalline aluminosilicate is 20% by mass or more, the total yield of the monocyclic aromatic hydrocarbons having a carbon number of 6 to 8 and the aliphatic hydrocarbons having a carbon number of 3 to 4 is sufficiently raised. When the content of the crystalline aluminosilicate exceeds 60% by mass, the content of a binder that may be mixed with the catalyst becomes small, and thus may be not appropriate as the catalyst for the fluidized bed.

In the crystalline aluminosilicate, a mass ratio of the large-pore zeolite to the intermediate-pore zeolite (large-pore zeolite/intermediate-pore zeolite) is preferably 2/98 to 50/50, more preferably 5/95 to 50/50, still more preferably 10/90 to 30/70. When the mass ratio is 2/98 or more, an effect of using the large-pore zeolite is sufficiently exhibited, and thus the yield of the monocyclic aromatic hydrocarbons is sufficiently raised. When the mass ratio is 50/50 or less, coking of the feedstock is prevented, and thus the yield of the monocyclic aromatic hydrocarbons is sufficiently raised.

(Other Components)

The catalyst may contain gallium and/or zinc as necessary. When gallium and/or zinc are contained, a generation ratio of the monocyclic aromatic hydrocarbons having a carbon number of 6 to 8 tends to be increased.

As a method used to incorporate gallium into the catalyst, a type in which gallium is incorporated in a lattice framework of the crystalline aluminosilicate (crystalline aluminogallosilicate), a type in which gallium is carried by the crystalline aluminosilicate (gallium-supporting crystalline aluminosilicate), and a type including both of these types is exemplified.

As a method used to incorporate zinc into the catalyst, a type in which zinc is incorporated in a lattice framework of the crystalline aluminosilicate (crystalline aluminozincosilicate), a type in which zinc is carried by the crystalline aluminosilicate (zinc-supporting crystalline aluminosilicate), and a type including both of these types is exemplified.

The crystalline aluminogallosilicate and the crystalline aluminozincosilicate have a structure in which $SiO_4$, $AlO_4$, and $GaO_4/ZnO_4$ structures have a tetrahedral coordination in a framework. In addition, the crystalline aluminogallosilicate and the crystalline aluminozincosilicate may be obtained, for example, by gel crystallization through hydrothermal synthesis, by a method in which gallium or zinc is inserted into the lattice framework of the crystalline aluminosilicate, or by a method in which aluminum is inserted into the lattice framework of crystalline gallosilicate or crystalline zincosilicate.

The gallium-supporting crystalline aluminosilicate may be obtained by supporting gallium on a crystalline aluminosilicate using a conventional method such as an ion-exchange method or impregnation method. There are no particular limitations on the gallium source used in these methods, and examples include gallium salts such as gallium nitrate and gallium chloride, and gallium oxide.

The zinc-supporting crystalline aluminosilicate may be obtained by supporting zinc on a crystalline aluminosilicate using a known method such as an ion-exchange method or impregnation method. There are no particular limitations on the zinc source used in these methods, and examples include zinc salts such as zinc nitrate and zinc chloride, and zinc oxide.

In a case where the catalyst contains gallium and/or zinc, the lower limit of the content of gallium and/or zinc is preferably 0.01% by mass or more on the basis of 100% by mass of the total mass of the crystalline aluminosilicate, and more preferably 0.05% by mass or more. On the other hand, the upper limit thereof is preferably 5.0% by mass or less, and more preferably 1.5% by mass or less. When the content of gallium and/or zinc is 0.01% by mass or more, a generation ratio of the monocyclic aromatic hydrocarbons having a carbon number of 6 to 8 is relatively raised. When the content thereof exceeds 5.0% by mass, a generated amount of coke is increased, and thus the yield of the monocyclic aromatic hydrocarbons having a carbon number of 6 to 8 is lowered. Therefore, this case is not preferable.

The catalyst may contain phosphorus and/or boron as necessary. When phosphorus and/or boron is contained, a decrease with the passage of time in the total yield of the monocyclic aromatic hydrocarbons having a carbon number of 6 to 8 and the aliphatic hydrocarbon having a carbon number of 3 to 4 may be prevented, and the coke may be prevented from being generated on the surface of the catalyst.

There are no particular limitations on a method of incorporating phosphorus in the catalyst, and examples thereof include a method in which phosphorus is made to be supported on crystalline aluminosilicate, crystalline aluminogallosilicate, or crystalline aluminozincosilicate by using an ion-exchange method, impregnation method, or the like, a method in which a phosphorus compound is incorporated during synthesis of the zeolite, and a part in the framework of the crystalline aluminosilicate is substituted with phosphorus, a method in which a crystallization promoter containing phosphorus is used during synthesis of the zeolite, and the like. Although there are no particular limitations on a phosphate ion-containing aqueous solution used at that time, a solution, which is prepared by dissolving phosphoric acid, diammonium hydrogen phosphate, ammonium dihydrogen phosphate, or another water-soluble phosphate salt in water at an arbitrary concentration, is preferably used.

There are no particular limitations on a method of incorporating boron in the catalyst, and examples thereof include a method in which boron is made to be supported on crystalline aluminosilicate, crystalline aluminogallosilicate, or crystalline aluminozincosilicate by using an ion-exchange method, impregnation method, or the like, a method in which a boron compound is incorporated during synthesis of the zeolite, and a part in the framework of the crystalline aluminosilicate is substituted with boron, a method in which a crystallization promoter containing boron is used during synthesis of the zeolite, and the like.

In a case where the catalyst contains phosphorus and/or boron, the lower limit of the content of phosphorus and/or boron is preferably 0.1% by mass or more on the basis of 100% by mass of the total mass of the crystalline aluminosilicate, and more preferably 0.2% by mass or more. On the other hand, the upper limit thereof is preferably 5.0% by mass or less, and more preferably 3.0% by mass or less. When the content of phosphorus and/or boron is 0.1% by mass or more, a decrease with the passage of time in the yield is further prevented. When the content thereof exceeds 5.0% by mass, the yield of the monocyclic aromatic hydrocarbons having a carbon number of 6 to 8 is lowered, and thus this is not preferable.

(Form)

The catalyst has a powder form, a granular form, or a pellet form, or the like depending on a reaction format. For example, in the case of a fluidized bed, the catalyst has the powder form, whereas in the case of a fixed bed, the catalyst has the granular form or the pellet form.

In the case of obtaining the catalyst having the granular form or the pellet form, an oxide inactive to the catalyst is mixed with the catalyst as a binder as necessary, and then the resultant mixture is molded with various types of molding machine.

In a case where the catalyst of this embodiment contains a binder or the like, the binder containing phosphorus and/or boron can be used. At this time, in the catalyst, the content of phosphorus and/or boron that are contained in the crystalline aluminosilicate (% by mass of phosphorus and/or boron on the basis of 100% by mass of the total mass of the crystalline aluminosilicate) is preferably 0.1 to 5.0% by mass. An amount of phosphorus and/or boron that are contained in the crystalline aluminosilicate represents an amount of phosphorus and/or boron that act on the crystalline aluminosilicate.

In addition, in a case where the catalyst contains a binder or the like, the catalyst is produced by mixing the binder or the like, and gallium and/or zinc supporting crystalline aluminosilicate or crystalline aluminogallosilicate and/or crystalline aluminozincosilicate, and then adding phosphorus and/or boron to the resulting mixture. At this time, in the catalyst, the content of phosphorus and/or boron that are contained in the crystalline aluminosilicate (% by mass of phosphorus and/or boron on the basis of 100% by mass of the total mass of the crystalline aluminosilicate) is preferably 0.1 to 5.0% by mass.

As the binder or the like that is mixed with the catalyst, an inorganic oxide is used, and as the binder or the like, a material containing phosphorus and/or boron can be used. By also considering the amount of phosphorus and/or boron that act on the crystalline aluminosilicate in the case of using the binder or the like that contains phosphorus and/or boron, it is preferable that the content of phosphorus and/or boron with respect to the total weight of the catalyst be 0.1 to 10% by mass, and the lower limit thereof be more preferably 0.5% by mass or more. The upper limit thereof is more preferably 9% by mass or less, and still more preferably 8% by mass or less. When the content of phosphorus and/or boron with respect to the total weight of the catalyst is 0.1% by mass or more, a decrease in the yield, over time, of the monocyclic aromatic hydrocarbon is prevented, and when the content is 10% by mass or less, the yield of the monocyclic aromatic hydrocarbon is raised.

(Method of Producing Monocyclic Aromatic Hydrocarbons)

The method of producing monocyclic aromatic hydrocarbons according to this embodiment is a method in which feedstock contacts with the above-mentioned catalyst to react with the other.

The reaction in this embodiment is a method in which acid points of the catalyst and the feedstock are brought into contact with each other, and through various reactions including decomposition, dehydrogenation, cyclization, hydrogen transfer, and the like, the polycyclic aromatic hydrocarbons are cleaved and are converted into monocyclic aromatic hydrocarbons having a carbon number of 6 to 8.

Here, the acid points are points which are, on a catalyst support, capable of releasing protons or capable of accepting electrons, and which are active points exhibiting acidity.

(Feedstock)

The feedstock that is used in this embodiment is oil in which a 10 vol % distillation temperature is 140° C. or higher and a 90 vol % distillation temperature is 380° C. or lower. In the oil in which the 10 vol % distillation temperature is lower than 140° C., BTX (Benzene, Toluene, and Xylene) is produced from light oil, and thus this does not match with the gist of this embodiment. In addition, in the case of using oil in which the 90 vol % distillation temperature is higher than 380° C., the yield of the monocyclic aromatic hydrocarbons is low and an amount of deposited coke on the catalyst increases, such that there is a tendency for activity of the catalyst to rapidly decrease.

It is preferable that the 10 vol % distillation temperature of the feedstock be 150° C. or higher and the 90 vol % distillation temperature of the feedstock be 380° C. or lower.

In addition, the 10 vol % distillation temperature and the 90 vol % distillation temperature described here represent values that are measured in accordance with JIS K2254 "Petroleum Products-Distillation Test Method"

As the feedstock in which the 10 vol % distillation temperature is 140° C. or higher and the 90 vol % distillation temperature is 380° C. or lower, for example, LCO produced by a fluid catalytic cracking unit, coal liquefaction oil, hydrocracked refined oil from heavy oil, straight-run kerosene, straight-run light oil, coker kerosene, coker light oil, and hydrocracked refined oil from oil sands may be exemplified.

In addition, when the feedstock contains a large amount of polycyclic aromatic hydrocarbons, the yield of monocyclic aromatic hydrocarbons having a carbon number of 6 to 8 tends to decrease, and therefore the content of polycyclic aromatic hydrocarbons (the polycyclic aromatic content) in the feedstock is preferably 50% by volume or less, and more preferably 30% by volume or less.

In addition, the polycyclic aromatic content described here represents the total value of the content of bicyclic aromatic hydrocarbons (the bicyclic aromatic content) and the content of tricyclic or higher aromatic hydrocarbons (the tricyclic or higher aromatic content) measured in accordance with JPI-5S-49 "Petroleum Products—Determination of Hydrocarbon Types—High Performance Liquid Chromatography".

(Reaction Format)

Examples of the reaction format used for bringing the feedstock into contact with the catalyst for reaction include a fixed bed, a moving bed and a fluidized bed. In this embodiment, since a heavy oil fraction is used as the raw material, the fluidized bed is preferable as it enables the coke fraction adhered to the catalyst to be removed in a continuous manner and enables the reaction to proceed in a stable manner. A continuous regeneration-type fluidized bed, in which the catalyst is circulated between a reactor and a regenerator, and thus a reaction-regeneration cycle is continuously repeated, is more preferable. The feedstock when being brought into contact with the catalyst is preferably in a gaseous state. Furthermore, the raw material is preferably diluted with a gas as necessary. Furthermore, in a case where unreacted raw material occurs, this may be recycled as necessary.

(Reaction Temperature)

Although there are no particular limitations on the reaction temperature during contact of the feedstock with the catalyst for reaction, a reaction temperature is preferably 350 to 700° C. In terms of achieving satisfactory reaction activity, the lower limit is more preferably 450° C. or higher. On the other hand, the upper limit temperature of 650° C. or lower is preferable as it is not only more advantageous from an energy perspective, but also enables easy regeneration of the catalyst.

(Reaction Pressure)

The reaction pressure during contact of the feedstock with the catalyst for reaction is preferably 1.0 MPaG or lower. When the reaction pressure is 1.0 MPaG or lower, the generation of by-product light gases may be prevented, and the pressure resistance required for a reaction device may be lowered.

(Contact Time)

There are no particular limitations on the contact time between the feedstock and the catalyst as long as a desired reaction actually proceeds, but in terms of the gas transit time across the catalyst, a time of 1 to 300 seconds is preferable. The lower limit for this time is more preferably 5 seconds or more, and the upper limit is more preferably 60 seconds or less. When the contact time is 1 second or more, reliable reaction is achieved, and when the contact time is 300 seconds or less, deposition of carbonaceous matter on the catalyst due to coking or the like is suppressed. Furthermore, the amount of light gas generated by cracking may also be suppressed.

In the method of producing the monocyclic aromatic hydrocarbons according to this reaction, by contacting the feedstock with acid points of the catalyst, and through various reactions including decomposition, dehydrogenation, cyclization, hydrogen transfer, and the like, the polycyclic aromatic hydrocarbons are cleaved and monocyclic aromatic hydrocarbons having a carbon number of 6 to 8 are obtained.

In this embodiment, the yield of monocyclic aromatic hydrocarbons is preferably 25% by mass or more, more preferably 30% by mass or more, and still more preferably 40% by mass or more. It is not preferable that the yield of monocyclic aromatic hydrocarbons is lower than 25% by mass, because the low concentration of the desired products in a reaction mixture causes low recovery efficiency.

EXAMPLES

Hereinafter, the embodiment will be described in detail on the basis of examples and comparative examples, but this embodiment is not limited to these examples.

(Preparation of Proton-Type MFI Zeolite)

A solution (A) composed of 1706.1 g of sodium silicate (J Sodium Silicate No. 3, $SiO_2$: 28 to 30% by mass, Na: 9 to 10% by mass, remainder is water; manufactured by Nippon Chemical Industrial Co., Ltd.) and 2227.5 g of water, and a solution (B) composed of 64.2 g of $Al_2(SO_4)_3 \cdot 14$ to $18H_2O$ (special reagent grade, manufactured by Wako Pure Chemical Industries, Ltd.), 369.2 g of tetrapropylammonium bromide, 152.1 g of $H_2SO_4$ (97% by mass), 326.6 g of NaCl, and 2975.7 g of water were prepared independently.

Subsequently, the solution (B) was added gradually to the solution (A) while the solution (A) was continuously stirred at room temperature. The resultant mixture was stirred vigorously for 15 minutes using a mixer, thereby breaking up the gel and forming a uniform fine milky state.

Then, this mixture was placed in a stainless steel autoclave, and a crystallization operation was performed under conditions including a temperature of 165° C., a reaction time of 72 hours, a stirring rate of 100 rpm, and under self-generated pressure. After the crystallization operation was completed, the resultant product was filtered, the solid product was recovered, and the washing and filtering of the solid product was repeated 5 times using approximately 5 liters of deionized water. The solid material obtained by the filtering was dried at 120° C., and was then baked under a stream of air at a high temperature of 550° C. for 3 hours.

From a result of X-ray diffraction analysis (apparatus model: Rigaku RINT-2500V) on the resultant baked product, it was confirmed that the product had a MFI structure. Furthermore, from fluorescent X-ray analysis (apparatus model: Rigaku ZSX101e), it was revealed that a $SiO_2/Al_2O_3$ ratio (molar ratio) was 64.8. In addition, based on these results, the amount of aluminum element incorporated in the lattice framework was calculated as 1.32% by mass.

A 30% by mass aqueous solution of ammonium nitrate was added to the obtained baked product in a ratio of 5 mL of the aqueous solution per 1 g of the baked product, the resultant mixture was heated at 100° C. while being stirred for 2 hours, and then the mixture was filtered and washed with water. This operation was repeated 4 times, and then the product was dried for 3 hours at 120° C., thereby obtaining an ammonium-type MFI zeolite. Subsequently, the product was baked for 3 hours at 780° C., thereby obtaining a proton-type MFI zeolite.

(Preparation of BEA-Type Zeolite)

BEA-type zeolite was prepared as described below according to a hydrothermal synthesis method in the related art.

59.1 g of a silicic acid ($SiO_2$: 89% by mass) was dissolved in 202 g of tetraethylammonium hydroxide aqueous solution (40% by mass) to prepare a first solution. This solution was added to a second solution that was prepared by solving 0.74 g of Al-pellets and 2.69 g of sodium hydroxide in 17.7 g of water.

The two solutions were mixed, thereby obtaining a reaction mixture having a composition (in terms of molar ratio of oxides) of 2.4 $Na_2O$-20.0 $(TEA)_2$-$Al_2O_3$-64.0 $SiO_2$-612$H_2O$. This reaction mixture was placed in a 0.3 L autoclave, and was heated at 150° C. for 6 days. The obtained product was separated from the mother liquid and the separated product was cleaned with distilled water. From a result of X-ray diffraction analysis (apparatus model: Rigaku RINT-2500V) on the product, BEA-type zeolite was confirmed from XRD patterns.

Then, after being subjected to ion-exchange using ammonium nitrate aqueous solution (30% by mass), the BEA-type zeolite was baked at 550° C. for 3 hours, whereby proton-type BEA zeolite was obtained.

(Preparation of FAU-Type Zeolite)

FAU-type zeolite was prepared as described below according to a hydrothermal synthesis method in the related art.

3 g of sodium aluminate containing 30.0% by mass of $Na_2O$, 44.1% by mass of $Al_2O_3$, and 25.9% by mass of $H_2O$, and 16.4 g of sodium hydroxide containing 77.5% by mass of $Na_2O$ were dissolved in 131 ml of deionized water. This resultant solution was added to 74.5 g of aqueous colloidal silica sol containing 29.5% by mass of silica, and these two solutions were mixed, thereby obtaining a reaction mixture having a composition (in terms of molar ratio of oxides) of 16.9 $Na_2O$—$Al_2O_3$-28.2 $SiO_2$-808$H_2O$. This mixture was mixed and stirred until it reached a uniform state, and this reaction mixture was placed in a 0.3 L autoclave, and was heated at 120° C. for 3 hours. The obtained product was separated from the mother liquid and the separated product was cleaned with distilled water. From a result of X-ray diffraction analysis (apparatus model: Rigaku RINT-2500V) on the product, FAU-type zeolite (Y-type zeolite) was confirmed from XRD patterns.

Then, after being subjected to ion-exchange using ammonium nitrate aqueous solution (30% by mass), the FAU-type zeolite was baked at 550° C. for 3 hours, whereby proton-type FAU zeolite was obtained. Then, this FAU-type zeolite was treated under vapor at a temperature of 650° C. to stabilize this zeolite, whereby stabilized proton-type FAU zeolite (USY zeolite) was prepared.

(Preparation of MOR-Type Zeolite)

MOR-type zeolite was prepared as described below according to a hydrothermal synthesis method in the related art.

2.7 g of sodium aluminate containing 30.0% by mass of $Na_2O$, 44.1% by mass of $Al_2O_3$, and 25.9% by mass of $H_2O$, and 6.3 g of sodium hydroxide were dissolved in 200 ml of deionized water. This resultant solution was added to 241 cc of aqueous colloidal silica sol containing 27.8% by mass of silica, thereby obtaining a reaction mixture having a composition (in terms of molar ratio of oxides) of 1.9 $Na_2O$—$Al_2O_3$-13 $SiO_2$. This mixture was mixed and stirred until it reached a uniform state, and this reaction mixture was placed in a 0.3 L autoclave, and was heated at 150° C. for 8 hours. The obtained product was separated from the mother liquid and the separated product was cleaned with distilled water. From a result of X-ray diffraction analysis (apparatus model: Rigaku RINT-2500V) on the product, MOR-type zeolite was confirmed from XRD patterns.

Then, after being subjected to ion-exchange using ammonium nitrate aqueous solution (30% by mass), the MOR-type zeolite was baked at 550° C. for 3 hours, whereby proton-type MOR zeolite was obtained. Then, this MOR zeolite was treated under vapor at a temperature of 650° C. to stabilize this zeolite, whereby stabilized proton-type MOR zeolite was prepared.

Example 1

A mixture in which 49 g of the proton-type MFI zeolite, and 1 g of the proton-type BEA zeolite were mixed was tablet-molded while applying a pressure of 39.2 MPa (400 kgf), and then the resultant tablets were coarsely crushed to have a uniform size of 20 to 28 mesh, whereby a granulated Catalyst 1 was obtained.

Feedstock having properties shown in Table 1 and the catalyst were made to come into contact and react with each other under conditions of a reaction temperature of 550° C. and a reaction pressure of 0 MPaG by using a flow type reaction device in which 10 ml of the Catalyst 1 was filled in a reactor thereof. At this time, nitrogen as a diluting agent was introduced in order for the contact time between the feedstock and the catalyst to be 6.4 seconds. Under this condition, reaction was carried out for 30 minutes, and thereby monocyclic aromatic hydrocarbons having a carbon number of 6 to 8 were prepared. Then, composition analysis of the product was performed by an FID gas chromatography instrument that was directly connected to the reaction device and the yield of the monocyclic aromatic hydrocarbon having a carbon number of 6 to 8 was measured. From this measurement, 42% by mass was confirmed. A measurement result is shown in Table 2.

TABLE 1

| Properties of raw material | | | | Analysis method |
|---|---|---|---|---|
| Density (@15° C.) | | g/cm³ | 0.906 | JIS K 2249 |
| Kinetic viscosity(@30° C.) | | mm²/s | 3.640 | JIS K 2283 |
| Distillation properties | Initial distillation point | ° C. | 175.5 | JIS K 2254 |
| | 10 vol % distillation temperature | ° C. | 224.5 | |
| | 50 vol % distillation temperature | ° C. | 274.0 | |
| | 90 vol % distillation temperature | ° C. | 349.5 | |
| | End point | ° C. | 376.0 | |
| Compositional analysis | Saturated portion | % by volume | 35 | JPI-5S-49 |
| | Olefin portion | % by volume | 8 | |
| | Total aromatic portion | % by volume | 57 | |
| | Monocyclic aromatic portion | % by volume | 23 | |
| | Bicyclic aromatic portion | % by volume | 25 | |
| | Tricyclic aromatic portion | % by volume | 9 | |

Example 2

A mixture in which 45 g of the proton-type MFI zeolite, and 5 g of the proton-type BEA zeolite were mixed was tablet-molded while applying a pressure of 39.2 MPa (400 kgf), and then the resultant tablets were coarsely crushed to have a uniform size of 20 to 28 mesh, whereby a granulated Catalyst 2 was obtained.

In addition, the yield of the monocyclic aromatic hydrocarbons having a carbon number of 6 to 8 was measured by using the Catalyst 2 in place of the Catalyst 1 in Example 1. From the measurement, 45% by mass was confirmed. A measurement result is shown in Table 2.

Example 3

A mixture in which 35 g of the proton-type MFI zeolite, and 15 g of the proton-type BEA zeolite were mixed was tablet-molded while applying a pressure of 39.2 MPa (400 kgf), and then the resultant tablets were coarsely crushed to have a uniform size of 20 to 28 mesh, whereby a granulated Catalyst 3 was obtained.

In addition, the yield of the monocyclic aromatic hydrocarbons having a carbon number of 6 to 8 was measured by using the Catalyst 3 in place of the Catalyst 1 in Example 1. From the measurement, 43% by mass was confirmed. A measurement result is shown in Table 2.

Example 4

A mixture in which 25 g of the proton-type MFI zeolite, and 25 g of the proton-type BEA zeolite were mixed was tablet-molded while applying a pressure of 39.2 MPa (400 kgf), and then the resultant tablets were coarsely crushed to have a uniform size of 20 to 28 mesh, whereby a granulated Catalyst 4 was obtained.

In addition, the yield of the monocyclic aromatic hydrocarbons having a carbon number of 6 to 8 was measured by using the Catalyst 4 in place of the Catalyst 1 in Example 1. From the measurement, 36% by mass was confirmed. A measurement result is shown in Table 2.

Examples 5 to 7

The yield of the monocyclic aromatic hydrocarbons having a carbon number of 6 to 8 was measured in the same way as Examples 2 to 4 except that the reaction temperature in Examples 2 to 4 was changed to 500° C. From the measurement, 45% by mass in Example 5, 43% by mass in Example 6, and 37% by mass in Example 7 were confirmed, respectively. A measurement result is shown in Table 2.

Comparative Example 1

50 g of the proton-type BEA zeolite was tablet-molded while applying a pressure of 39.2 MPa (400 kgf), and then the resultant tablets were coarsely crushed to have a uniform size of 20 to 28 mesh, whereby a granulated Catalyst 5 was obtained.

In addition, the yield of the monocyclic aromatic hydrocarbons having a carbon number of 6 to 8 was measured by using the Catalyst 5 in place of the Catalyst 1 in Example 1. From the measurement, 21% by mass was confirmed. A measurement result is shown in Table 2.

TABLE 2

| | Example 1 | Example 2 | Example 3 | Example 4 | Example 5 | Example 6 | Example 7 | Comparative Example 1 |
|---|---|---|---|---|---|---|---|---|
| Catalyst | Catalyst 1 | Catalyst 2 | Catalyst 3 | Catalyst 4 | Catalyst 2 | Catalyst 3 | Catalyst 4 | Catalyst 5 |
| BEA zeolite/MFI zeolite (mass ratio) | 2/98 | 10/90 | 30/70 | 50/50 | 10/90 | 30/70 | 50/50 | 100/0 |
| Reaction temperature (° C.) | | | 550 | | | 500 | | 550 |
| Yield of monocyclic hydrocarbons (% by mass) | 42 | 45 | 43 | 36 | 45 | 43 | 37 | 21 |

(Results)

In Examples 1 to 7 using the catalysts 1 to 4 containing both of the BEA-type zeolite and the MFI-type zeolite, the monocyclic aromatic hydrocarbons having a carbon number of 6 to 8 were obtained with high yield.

Conversely, in Comparative Example 1 using the Catalyst 5 composed of only the BEA-type zeolite, the yield of the monocyclic aromatic hydrocarbons having a carbon number of 6 to 8 was low.

Example 8

30 g of a mixture in which 35 g of the proton-type MFI zeolite and 15 g of the proton-type BEA zeolite were mixed was impregnated with 30 g of gallium nitrate aqueous solution in order for 0.4% by mass (on the basis of 100% by mass of the total mass of the mixture of the proton-type MFI zeolite and the proton-type BEA zeolite) of gallium to be supported, and then the resultant mixture was dried at 120° C. Then, the resultant dried product was baked under a stream of air at a high temperature of 780° C. for 3 hours, whereby gallium-supporting crystalline aluminosilicate was obtained. This gallium-supporting crystalline aluminosilicate was tablet-molded while applying a pressure of 39.2 MPa (400 kgf), and then the resultant tablets were coarsely crushed to have a uniform size of 20 to 28 mesh, whereby a granulated Catalyst 6 was obtained.

In addition, the yield of the monocyclic aromatic hydrocarbons having a carbon number of 6 to 8 was measured by using the Catalyst 6 in place of the catalyst 1 in Example 1. From the measurement, 44% by mass was confirmed. A measurement result is shown in Table 3.

Example 9

30 g of a mixture in which 35 g of the proton-type MFI zeolite and 15 g of the proton-type BEA zeolite were mixed was impregnated with 30 g of zinc nitrate aqueous solution in order for 0.4% by mass (on the basis of 100% by mass of the total mass of the mixture of the proton-type MFI zeolite and the proton-type BEA zeolite) of zinc to be supported, and then the resultant mixture was dried at 120° C. Then, the resultant dried product was baked under a stream of air at a high temperature of 780° C. for 3 hours, whereby zinc-supporting crystalline aluminosilicate was obtained. This zinc-supporting crystalline aluminosilicate was tablet-molded while applying a pressure of 39.2 MPa (400 kgf), and then the resultant tablets were coarsely crushed to have a uniform size of 20 to 28 mesh, whereby a granulated Catalyst 7 was obtained.

In addition, the yield of the monocyclic aromatic hydrocarbons having a carbon number of 6 to 8 was measured by using the Catalyst 7 in place of the Catalyst 1 in Example 1. From the measurement, 44% by mass was confirmed. A measurement result is shown in Table 3.

TABLE 3

| | Example 8 | Example 9 |
|---|---|---|
| Catalyst | Catalyst 6 | Catalyst 7 |
| BEA zeolite/MFI zeolite (mass ratio) | 30/70 | 30/70 |
| Kinds of supporting metal | Gallium | Zinc |
| Content of gallium or zinc (% by mass) | 0.4 | 0.4 |
| Yield of monocyclic aromatic hydrocarbons (% by mass) | 44 | 44 |

(Result)

In Examples 8 and 9 using the catalysts 6 and 7 in which gallium or zinc was supported on the zeolite in which the BEA-type zeolite and the MFI-type zeolite were mixed, the monocyclic aromatic hydrocarbons having a carbon number of 6 to 8 were obtained with high yield.

Example 10

The Catalyst 3 was subjected to a hydrothermal treatment under an environment of a treatment temperature of 650° C., a treatment time of 6 hours, and 100% by mass of vapor to obtain a pseudo-degraded Catalyst 3 that was hydrothermally degraded in a pseudo manner.

The feedstock was subjected to reaction similarly to Example 1 except that the pseudo-degraded Catalyst 3 was used in place of the Catalyst 1, and composition analysis of the obtained product was performed to evaluate the catalyst activity after the hydrothermal degradation. In the case of using the pseudo-degraded Catalyst 3, 18% by mass of the monocyclic aromatic hydrocarbons having a carbon number of 6 to 8 was confirmed. An evaluation result is shown in Table 4.

Example 11

30 g of a mixture in which 35 g of the proton-type MFI zeolite and 15 g of the proton-type BEA zeolite were mixed was impregnated with 30 g of diammonium hydrogen phosphate aqueous solution in order for 2.0% by mass (on the basis of 100% by mass of the total mass of the mixture of the proton-type WI zeolite and the proton-type BEA zeolite) of phosphorus to be supported, and then the resultant mixture was dried at 120° C. Then, the resultant dried product was baked under a stream of air at a high temperature of 780° C. for 3 hours, whereby phosphorus-supporting crystalline aluminosilicate was obtained. This phosphorus-supporting crystalline aluminosilicate was tablet-molded while applying a pressure of 39.2 MPa (400 kgf), and then the resultant tablets were coarsely crushed to have a uniform size of 20 to 28 mesh, whereby a granulated Catalyst 8 was obtained.

Then, the Catalyst 8 was subjected to a hydrothermal treatment under an environment of a treatment temperature of 650° C., a treatment time of 6 hours, and 100% by mass of vapor to obtain a pseudo-degraded Catalyst 8 that was hydrothermally degraded in a pseudo manner.

The feedstock was subjected to reaction similarly to Example 1 except that the pseudo-degraded Catalyst 8 was used in place of the Catalyst 1, and composition analysis of the obtained product was performed to evaluate the catalyst activity after the hydrothermal degradation. In the case of using the pseudo-degraded Catalyst 8, 32% by mass of the monocyclic aromatic hydrocarbons having a carbon number of 6 to 8 was confirmed. An evaluation result is shown in Table 4.

Example 12

A mixture in which 35 g of the proton-type MFI zeolite, and 15 g of the stabilized proton-type FAU zeolite were mixed was tablet-molded while applying a pressure of 39.2 MPa (400 kgf), and then the resultant tablets were coarsely crushed to have a uniform size of 20 to 28 mesh, whereby a granulated Catalyst 9 was obtained.

Then, the Catalyst 9 was subjected to a hydrothermal treatment under an environment of a treatment temperature of 650° C., a treatment time of 6 hours, and 100% by mass of vapor to obtain a pseudo-degraded Catalyst 9 that was hydrothermally degraded in a pseudo manner.

The feedstock was subjected to reaction similarly to Example 1 except that the pseudo-degraded Catalyst 9 was used in place of the Catalyst 1, and composition analysis of the obtained product was performed to evaluate the catalyst activity after the hydrothermal degradation. In the case of using the pseudo-degraded Catalyst 9, 15% by mass of the monocyclic aromatic hydrocarbons having a carbon number of 6 to 8 was confirmed. An evaluation result is shown in Table 4.

Example 13

30 g of a mixture in which 35 g of the proton-type MFI zeolite and 15 g of the stabilized proton-type FAU zeolite were mixed was impregnated with 30 g of diammonium hydrogen phosphate aqueous solution in order for 2.0% by mass (on the basis of 100% by mass of the total mass of the mixture of the proton-type MFI zeolite and the stabilized proton-type FAU zeolite) of phosphorus to be supported, and then the resultant mixture was dried at 120° C. Then, the resultant dried product was baked under a stream of air at a high temperature of 780° C. for 3 hours, whereby phosphorus-supporting crystalline aluminosilicate was obtained. This phosphorus-supporting crystalline aluminosilicate was tablet-molded while applying a pressure of 39.2 MPa (400 kgf), and then the resultant tablets were coarsely crushed to have a uniform size of 20 to 28 mesh, whereby a granulated Catalyst 10 was obtained.

Then, the Catalyst 10 was subjected to a hydrothermal treatment under an environment of a treatment temperature of 650° C., a treatment time of 6 hours, and 100% by mass of vapor to obtain a pseudo-degraded Catalyst 10 that was hydrothermally degraded in a pseudo manner.

The feedstock was subjected to reaction similarly to Example 1 except that the pseudo-degraded Catalyst 10 was used in place of the Catalyst 1, and composition analysis of the obtained product was performed to evaluate the catalyst activity after the hydrothermal degradation. In the case of using the pseudo-degraded Catalyst 10, 32% by mass of the monocyclic aromatic hydrocarbons having a carbon number of 6 to 8 was confirmed. An evaluation result is shown in Table 4.

Example 14

A mixture in which 35 g of the proton-type MFI zeolite, and 15 g of the stabilized proton-type MOR zeolite were mixed was tablet-molded while applying a pressure of 39.2 MPa (400 kgf), and then the resultant tablets were coarsely crushed to have a uniform size of 20 to 28 mesh, whereby a granulated Catalyst 11 was obtained.

Then, the Catalyst 11 was subjected to a hydrothermal treatment under an environment of a treatment temperature of 650° C., a treatment time of 6 hours, and 100% by mass of vapor to obtain a pseudo-degraded Catalyst 11 that was hydrothermally degraded in a pseudo manner.

The feedstock was subjected to reaction similarly to Example 1 except that the pseudo-degraded Catalyst 11 was used in place of the Catalyst 1, and composition analysis of the obtained product was performed to evaluate the catalyst activity after the hydrothermal degradation. In the case of using the pseudo-degraded Catalyst 11, 16% by mass of the monocyclic aromatic hydrocarbons having a carbon number of 6 to 8 was confirmed. An evaluation result is shown in Table 4.

Example 15

30 g of a mixture in which 35 g of the proton-type MFI zeolite and 15 g of the stabilized proton-type MOR zeolite were mixed was impregnated with 30 g of phosphoric acid aqueous solution in order for 2.0% by mass (on the basis of 100% by mass of the total mass of the mixture of the proton-type MFI zeolite and the stabilized proton-type MOR zeolite) of phosphorus to be supported, and then the resultant mixture was dried at 120° C. Then, the resultant dried product was baked under a stream of air at a high temperature of 780° C. for 3 hours, whereby phosphorus-supporting crystalline aluminosilicate was obtained. This phosphorus-supporting crystalline aluminosilicate was tablet-molded while applying a pressure of 39.2 M Pa (400 kgf), and then the resultant tablets were coarsely crushed to have a uniform size of 20 to 28 mesh, whereby a granulated Catalyst 12 was obtained.

Then, the Catalyst 12 was subjected to a hydrothermal treatment under an environment of a treatment temperature of 650° C., a treatment time of 6 hours, and 100% by mass of vapor to obtain a pseudo-degraded Catalyst 12 that was hydrothermally degraded in a pseudo manner.

The feedstock was subjected to reaction similarly to Example 1 except that the pseudo-degraded Catalyst 12 was used in place of the Catalyst 1, and composition analysis of the obtained product was performed to evaluate the catalyst activity after the hydrothermal degradation. In the case of using the pseudo-degraded Catalyst 12, 32% by mass of the monocyclic aromatic hydrocarbons having a carbon number of 6 to 8 was confirmed. An evaluation result is shown in Table 4.

(Result)

Even when the FAU-type zeolite or the MOR-type zeolite was used as the large-pore zeolite, substantially the same effect as the case of using the BEA-type zeolite was obtained.

Furthermore, when phosphorus was incorporated in the catalyst, monocyclic aromatic hydrocarbons having a carbon number of 6 to 8 were obtained with high yield even after the pseudo-degradation.

TABLE 4

|  | Example 10 | Example 11 | Example 12 | Example 13 | Example 14 | Example 15 |
|---|---|---|---|---|---|---|
| Catalyst | Pseudo-degraded catalyst 3 | Pseudo-degraded catalyst 8 | Pseudo-degraded catalyst 9 | Pseudo-degraded catalyst 10 | Pseudo-degraded catalyst 11 | Pseudo-degraded catalyst 12 |
| Kinds of large-pore zeolite | BEA | BEA | FAU | FAU | MOR | MOR |
| Kinds of intermediate-pore zeolite | MFI | MFI | MFI | MFI | MFI | MFI |
| Large-pore zeolite/ intermediate-pore zeolite (mass ratio) | 30/70 | 30/70 | 30/70 | 30/70 | 30/70 | 30/70 |

TABLE 4-continued

| | Example 10 | Example 11 | Example 12 | Example 13 | Example 14 | Example 15 |
|---|---|---|---|---|---|---|
| Content of phosphorus (% by mass) on the basis of 100% by mass of total mass of crystalline aluminosilicate | 0 | 2 | 0 | 2 | 0 | 2 |
| Yield of monocyclic aromatic hydrocarbons (% by mass) | 18 | 32 | 15 | 32 | 16 | 32 |

INDUSTRIAL APPLICABILITY

According to the catalyst for production of monocyclic aromatic hydrocarbons of the invention, monocyclic aromatic hydrocarbons having a carbon number of 6 to 8 may be produced with high efficiency from feedstock in which a 10 vol % distillation temperature is 140° C. or higher and a 90 vol % distillation temperature is 380° C. or lower.

The invention claimed is:

1. A method for producing monocyclic aromatic hydrocarbons having a carbon number of 6 to 8, the method comprising bringing feedstock in which a 10 vol % distillation temperature is 140° C. or higher and a 90 vol % distillation temperature is 380° C. or lower into contact with a catalyst comprising a large-pore zeolite having a 12-membered ring structure and an intermediate pore zeolite having a 10-membered ring structure, wherein
   a contact time between the feedstock and the catalyst is 5 seconds to 300 seconds,
   the yield of monocyclic aromatic hydrocarbons is 30% by mass or more, and
   a mass ratio of the large-pore zeolite to the intermediate-pore zeolite in the catalyst is 2/98 to 10/90.

2. The method for producing monocyclic aromatic hydrocarbons according to claim 1, wherein the feedstock comprises light cycle oil produced by a fluidized catalytic cracking unit.

3. The method for producing monocyclic aromatic hydrocarbons according to claim 1, wherein the feedstock is brought into contact with the catalyst in a fluidized bed reaction unit.

4. The method for producing monocyclic aromatic hydrocarbons according to claim 1, wherein the large-pore zeolite is selected from a BEA type, an FAU type, and an MOR type zeolite.

5. The method for producing monocyclic aromatic hydrocarbons according to claim 1, wherein the large-pore zeolite is a BEA-type zeolite.

6. The method for producing monocyclic aromatic hydrocarbons according to claim 1, wherein the intermediate-pore zeolite is an MFI-type zeolite.

7. The method of producing monocyclic aromatic hydrocarbons according to claim 1, wherein the catalyst further comprises phosphorus.

8. The method for producing monocyclic aromatic hydrocarbons according to claim 1, wherein the yield of monocyclic aromatic hydrocarbons is 40% by mass or more.

* * * * *